United States Patent [19]

Burns

[11] Patent Number: 5,552,117
[45] Date of Patent: *Sep. 3, 1996

[54] COLLECTION ASSEMBLY HAVING A CAP LIFTING MECHANISM

[75] Inventor: James A. Burns, Elizabeth, N.J.

[73] Assignee: Becton Dickinson and Company, Franklin Lakes, N.J.

[*] Notice: The term of this patent shall not extend beyond the expiration date of Pat. No. 5,384,096.

[21] Appl. No.: 236,288

[22] Filed: Apr. 29, 1994

[51] Int. Cl.$^6$ .................. A61B 5/14; B01L 3/14; B65D 41/18; C12M 1/24
[52] U.S. Cl. .................. 422/102; 422/99; 128/763; 128/767; 215/295; 215/318; 215/321; 215/354; 220/306; 435/307.1; 435/304.1; 494/16
[58] Field of Search ............... 128/760, 763–767; 215/208, 216, 219, 222, 224, 225, 252, 295, 317, 318, 321, 353, 354, 355, 332, 359; 220/306, 281; 422/99, 102; 435/296; 494/16

[56] References Cited

U.S. PATENT DOCUMENTS

| 2,193,226 | 3/1940 | Deletzke | 215/295 |
|---|---|---|---|
| 3,136,458 | 6/1964 | Ruetz | 220/306 X |
| 3,372,834 | 3/1968 | Ayotte et al. | 220/306 |
| 3,419,179 | 1/1968 | Deuschle et al. | 220/306 |
| 3,741,423 | 6/1973 | Acton et al. | 215/318 |
| 3,902,477 | 9/1975 | Gerarde | 215/355 X |
| 3,904,063 | 9/1975 | Hauser | 215/318 |
| 3,945,525 | 3/1976 | Jones | 215/295 X |
| 3,955,696 | 5/1976 | Finke | 215/318 X |
| 3,982,651 | 9/1976 | Braun et al. | 220/306 X |
| 4,051,974 | 10/1977 | Gentile | 220/306 X |
| 4,171,057 | 10/1979 | Gach | 215/295 X |
| 4,298,129 | 11/1981 | Stull | 215/318 X |
| 4,576,185 | 3/1986 | Proud et al. | 128/760 |
| 5,288,466 | 2/1994 | Burns | 422/102 |
| 5,384,096 | 1/1995 | Burns | 422/102 |

FOREIGN PATENT DOCUMENTS

| 517119 | 12/1992 | European Pat. Off. | 128/760 |
|---|---|---|---|
| 2063226 | 6/1981 | United Kingdom | 215/318 |

*Primary Examiner*—Arlen Soderquist
*Attorney, Agent, or Firm*—Alan W. Fiedler

[57] ABSTRACT

The present invention is a collection assembly useful for collecting small quantities of blood. The assembly comprises a container with an integral lip for facilitating collection of the blood and a cap suitable for enclosing the container. The assembly further comprises a sealing arrangement for securing the cap to the container using a protrusion on the cap and a locking ring on the container, wherein the container includes a riser below the locking ring that interacts with the protrusion on the cap to unsecure the cap from the container, when the cap is rotated on the container.

7 Claims, 6 Drawing Sheets

COLLECTION ASSEMBLY HAVING A CAP LIFTING MECHANISM

BACKGROUND OF THE INVENTION

1. Field of the Invention

The present invention relates to a collection assembly and, more particularly, to a microcollection container and cap suitable for collecting small quantities of blood from a patient and maintaining the blood in secure fashion for subsequent testing.

2. Description of Related Art

Analytical instrumentation has made it possible to carry out a variety of hematological diagnostic procedures on very small quantities of blood. Because of this, a patient's finger or earlobe, for example, may be punctured and a very small quantity of blood may be rapidly collected into a container for such testing. However, in order to carry out testing and analysis on small quantities of blood, the blood must be rapidly collected prior to any coagulation thereof.

A collection arrangement as described in U.S. Pat. No. 5,288,466, has been provided wherein a cap having a sealing element is configured to fit the top of a microcollection container having a lip for engaging the puncture site and transferring blood to the container. However, with such an arrangement, when a sample is taken, blood droplets may be left in and around the top area of the container or on the bottom of the sealing element. Therefore, excess blood may be aspirated when the cap is removed from the top of the container.

SUMMARY OF THE INVENTION

The present invention is a collection assembly comprising a container and a cap. The cap preferably comprises a closed top portion, an open bottom portion, and an annular skirt having an inner surface and an outer surface. The cap further includes an inner skirt portion generated from the closed top portion that does not extend as long as the annular skirt and is closed off at its extremity by a sealing ring. The sealing ring protrudes into an annular space between the two skirts. Desirably, the inside surface of the annular skirt comprises at least one protrusion. The cap further comprises a bottom stop ledge at the open end of the annular skirt and a shield that extends from the outer surface of the annular skirt.

The container preferably comprises an open top portion, a closed bottom portion, a sidewall extending from the top portion to the bottom portion and an open end associated with the top portion having an integral collector or lip portion. Most preferably the integral collector is a scoop that is the same diameter as the inner diameter of the container so that no air vent is required.

The container further includes a cap seating flange associated with the outer diameter of the top portion of the container, an extending annular skirt associated with the bottom portion, a locking ring associated between the integral collector and the cap seating flange, and a blood trap or trough positioned within the cap seating flange.

Preferably, the collection assembly includes means for securing the inner surfaces of the cap to the top portion of the container by the interaction of the protrusions of the cap with the locking ring of the container and the sealing ring of the cap with the inside surface of the top portion of the container. Most preferably, the collection assembly includes means for unsecuring the cap from the container including at least one riser located on the container between the locking ring and the cap seating flange that interacts with the protrusions on the cap to lift the protrusions over the locking ring on the container.

In a preferred embodiment of the invention, when the cap is placed on the container it is snap-sealed to the container by the interaction of the protrusions of the cap with the locking ring of the container and the sealing ring of the cap with the inside surface of the top portion of the container. This action, which may cause an audible-snap, in turn seals the container by compressing the protrusions of the cap against the underside of the locking ring of the container and the sealing ring of the cap against the inside surface of the top portion of the container to form a non-permanent lock and to substantially prevent the outer surface of the top portion of the container from making contact with the inside surface of the cap's annular skirt.

The cap and container also include means for easily unlocking the cap from the locking ring on the container that assist in substantially reducing fluid splatter from the container. Most preferably, to unlock the cap from the container, an upward rotational force is applied to the cap that causes the protrusion to climb up the riser and, in turn, release the protrusion from the locking ring which unlocks the cap from the container. An important advantage of the present invention is that the rotational force applied to the cap can be bi-directional, that is clockwise or counter-clockwise.

An advantage of the present invention is that any excess fluid on the outside surface of the integral collector will flow into the blood trap or trough of the cap seating flange as the cap and container are being secured. Therefore, radial spray of excess fluid is minimized and any excess fluid on the top of the cap seating flange will be directed downward between the outer diameter of the cap seating flange and the cap shield.

Still another advantage of the invention is that only the sealing-ring makes contact with fluid collected in the container. Therefore the inner surfaces of the cap may be minimally exposed to fluid collected in the container when the cap is secured to the top portion of the container and again radial spray of excess fluid is minimized during cap removal.

Another advantage of the present invention is that, when the cap is secured to the container, the flange on the container is not covered completely by the shield on the cap, so that when the capped assembly is centrifuged the load is on the flange and the cap is not loosened.

DETAILED DESCRIPTION

Figure 1:
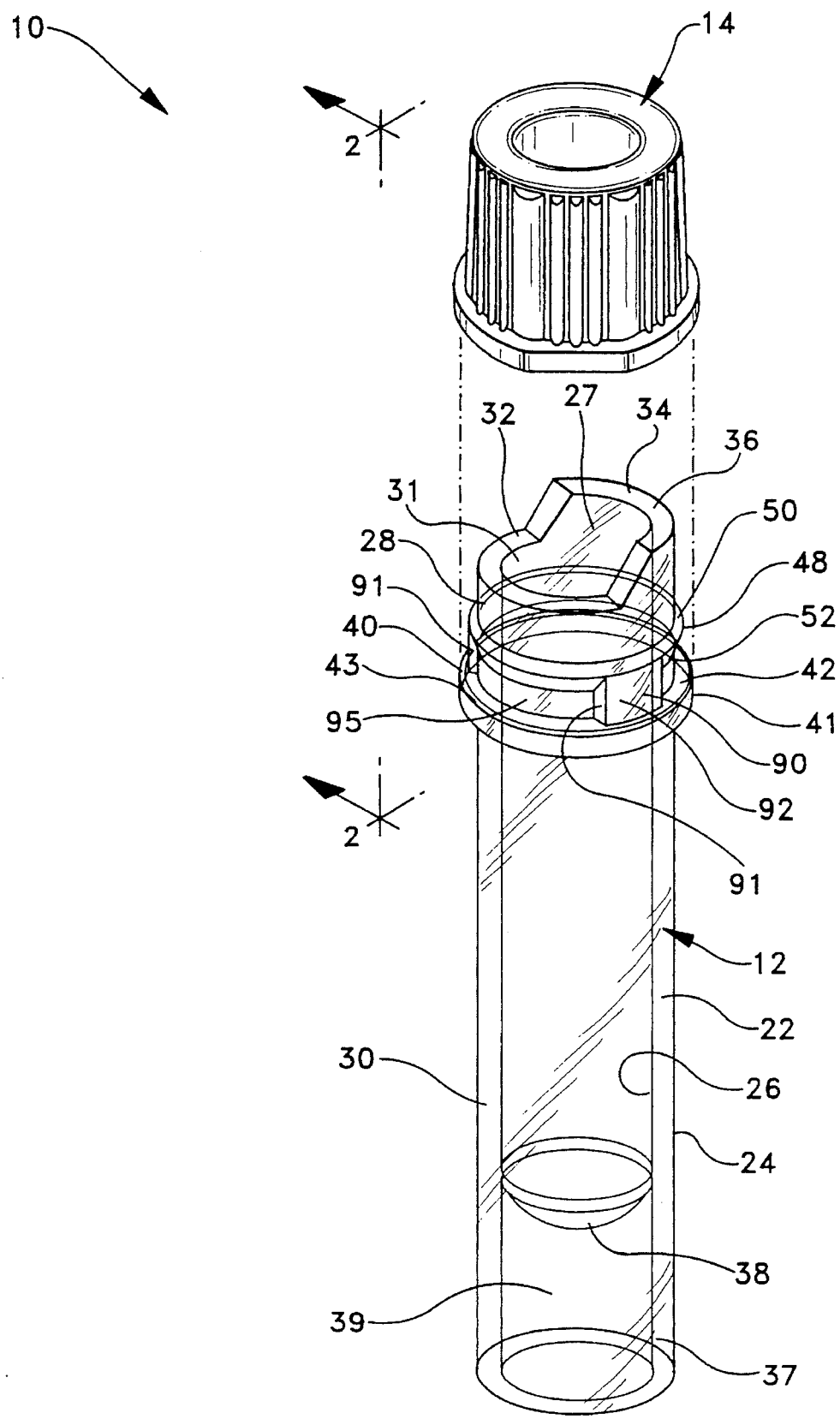
FIG. 1 is a perspective view of the preferred collection assembly illustrating the container with the cap unsecured.

Referring to the drawings in which like reference characters refer to like parts throughout the several views thereof, FIG. 1 is a perspective view of a preferred collection assembly 10 illustrating a container 12 with a cap 14 unsecured.

As illustrated in FIG. 1, container 12 has a sidewall 22 having an outer surface 24 and an inner surface 26. Sidewall 22 extends from an upper portion 28 to a lower portion 30. Upper portion 28 includes an open end 31 and an inner surface 27 with a top surface 32 having an integral lip portion 34 with a receiving edge 36. Lower portion 30 comprises a closed bottom end 38 and an annular skirt 37 extending from closed bottom end 38 to define a compartment area 39. Annular skirt 37 provides means for allowing container 12 to be placed upright on a flat surface and means for receiving cap 14 in compartment area 39.

Upper portion 28 has a cap seating flange 40 positioned around outer surface 24 of container 12 which defines a well or trough 42 having an outer wall 41 with an upper surface edge 43. Further positioned on upper portion 28 of container 12 is a locking ring 48 that is positioned between receiving edge 36 of integral lip portion 34 and cap seating flange 40. Locking ring 48 has an upper edge 50 and a lower edge 52. A plurality of risers 90 are positioned between locking ring 48 and cap seating flange 40, each riser 90 being separated from each other by an indent 95 and having a pair of inclines 91 on either side of a top surface 92. Top surface 92 being flush with the junction between upper edge 50 and lower edge 52 of locking ring 48.

Figure 2:
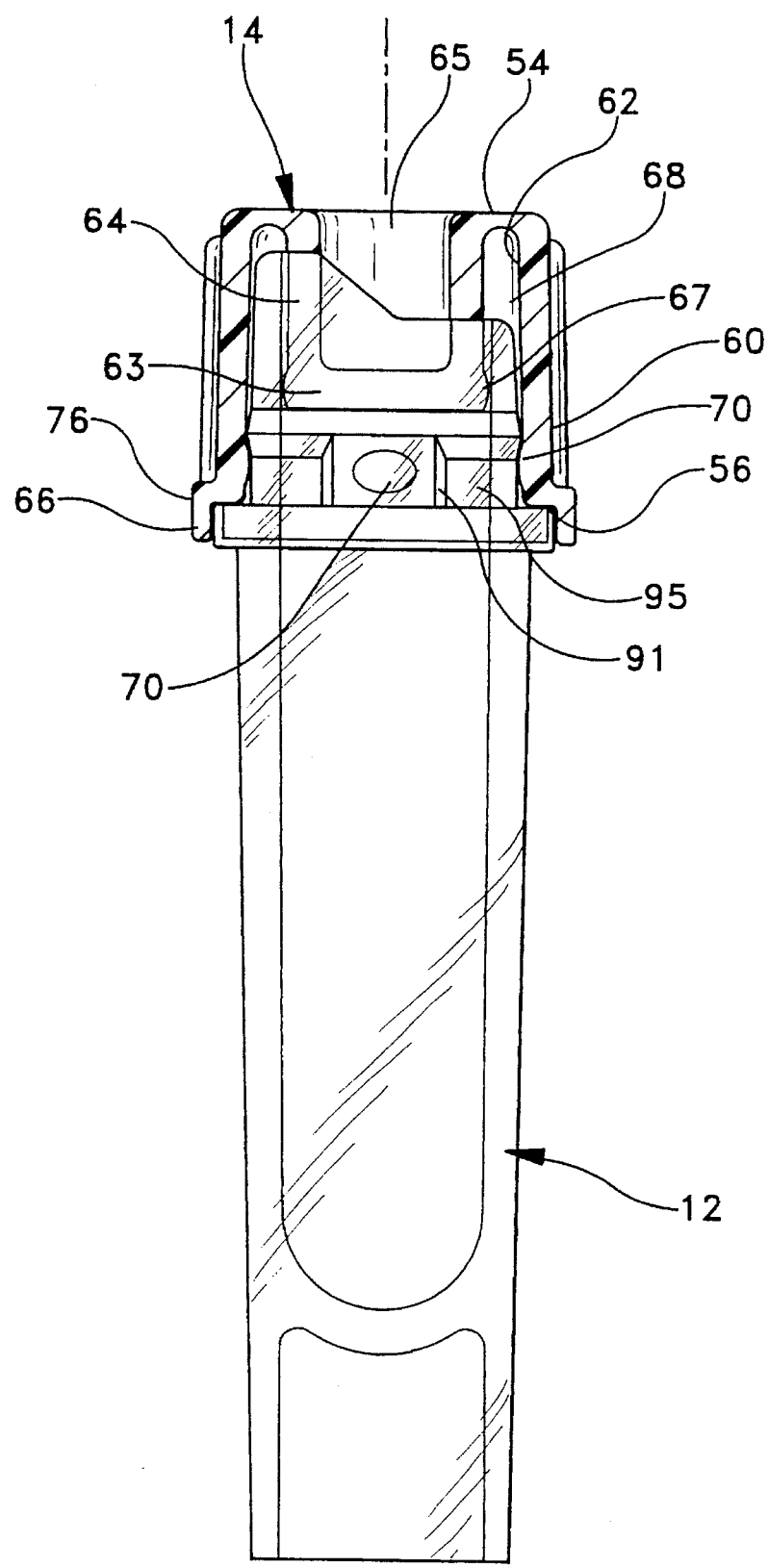
FIG. 2 is a side elevational view of the container of FIG. 1 with the cap secured thereto.

FIG. 2 is a side elevational view of container 12 with cap 14 secured thereto, and shows the interaction between container 12 and cap 14. Cap 14 includes a top surface 54, a bottom stop ledge 56 and an annular outer skirt 58 extending from top surface 54 to bottom stop ledge 56. Annular outer skirt 58 has an outer wall surface 60 and an inner wall surface 62, and a shield 66 extending from the bottom of outer wall surface 60 of annular outer skirt 58 having an outer surface or circumference 76.

As shown in FIG. 2, cap 14 also has an inner annular recessed skirt 64 that extends from top portion 54 to a bottom surface 63. Recessed skirt 64 defines a compartment or cup area 65 in top portion 54 of cap 14. Inner wall surface 62 of annular outer skirt 58 and inner annular recessed skirt 64 are spaced from each other to define an annular space 68. Cap 14 further includes a plurality of circumferentially spaced protrusions 70 positioned on inner wall surface 62 and a sealing ring 67 positioned on recessed skirt 64.

Figure 3:
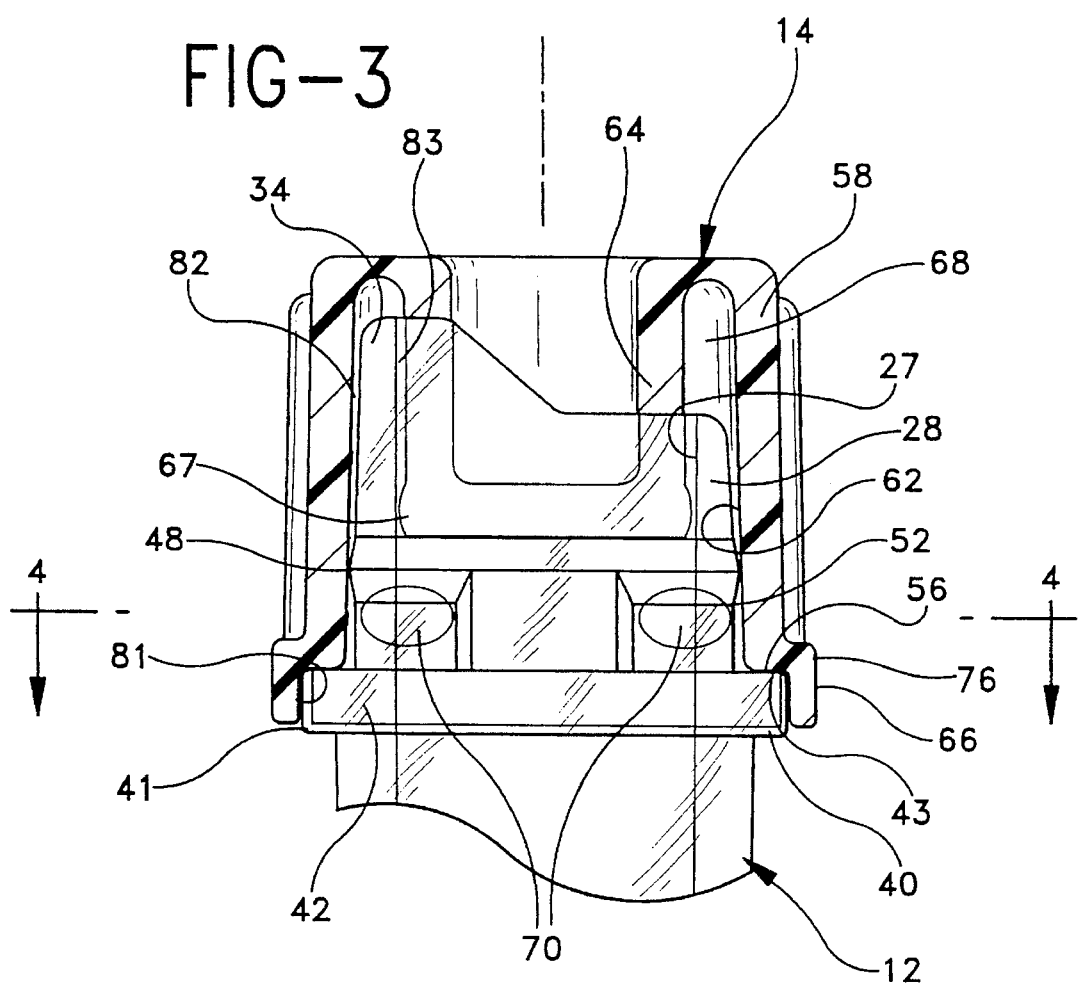
FIG. 3 is an enlarged cross-sectional view of the container and cap of FIG. 1, with the cap in the locked position.
Figure 4:
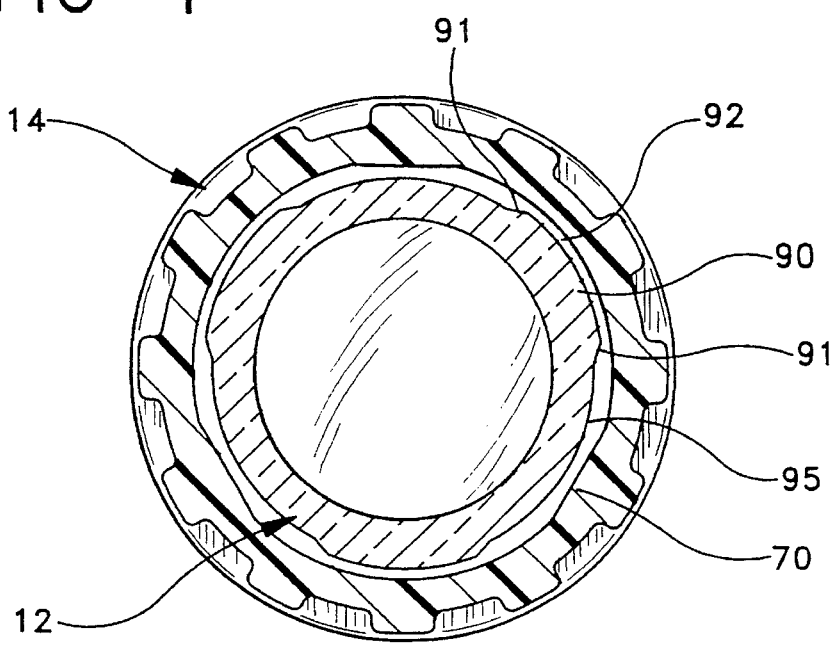
FIG. 4 is a cross-sectional view of the container and cap of FIG. 3, taken along line 4—4 thereof.

As shown in FIGS. 3 and 4, when cap 14 is removably secured to container 12, space 68 of cap 14 receives upper portion 28 of container 12 including integral lip portion 34, protrusions 70 bear against lower edge 52 of locking ring 48 of container 12 and sealing ring 67 bears against inner surface 27 of container 12. Shield 66 covers outer wall 41 of cap seating flange 40 and bottom stop ledge 56 abuts with upper surface edge 43 of cap seating flange 40, so as to form a non-permanent lock and substantially prevent any excess fluid in well 42 of cap seating flange 40 from spilling out. Any fluid that migrates between upper surface edge 43 and bottom stop ledge 56 is directed in a downward direction along container 12 by an inner surface 81 of shield 66 to minimize radial spray. In addition, spaces 82 and 83 remain between integral lip portion 34 and skirts 58 and 64, respectively, to prevent blood on lip portion 34 from being (i) wiped upward or splattered when cap 14 is removed from container 12 and (ii) pushed down towards bottom stop ledge 56 when cap 14 is secured to container 12. Further, any fluid in well 42 is substantially contained by upper surface edge 43 of cap seating flange 40 and bottom stop ledge 56 of cap 14. Outer surface 76 of shield 66 does not cover cap seating flange 40 of container 12 completely, as shown in FIG. 3, so that when the capped assembly is centrifuged the load is on flange 40 and cap 14 is not loosened.

As shown in FIGS. 3 and 4, cap 14 is snapped onto upper portion 28 of container 12 and is removably secured to container 12 by protrusions 70 and sealing ring 67 as they bear respectfully against lower edge 52 of locking ting 48 and inner surface 27 of container 12. The position of protrusions 70 in respective indents 95, as shown in FIG. 3 and the cross-sectional view in FIG. 4 taken along line 4—4 in FIG. 3, provide the locking action between container 12 and cap 14. In addition, the position of protrusions 70 and sealing ring 67 of cap 14 with container 12 forms space 82 between outer surface 24 of upper portion 28 and inner wall surface 62 of annular outer skirt 58. Therefore, wiping down of any fluid on the outer surface 24 of upper portion 28 is substantially prevented. In addition, bottom stop edge 56 bears against flange upper surface 43 to provide a stop and insure a proper sealing depth for sealing ring 67 on inner surface 27.

Figure 5:
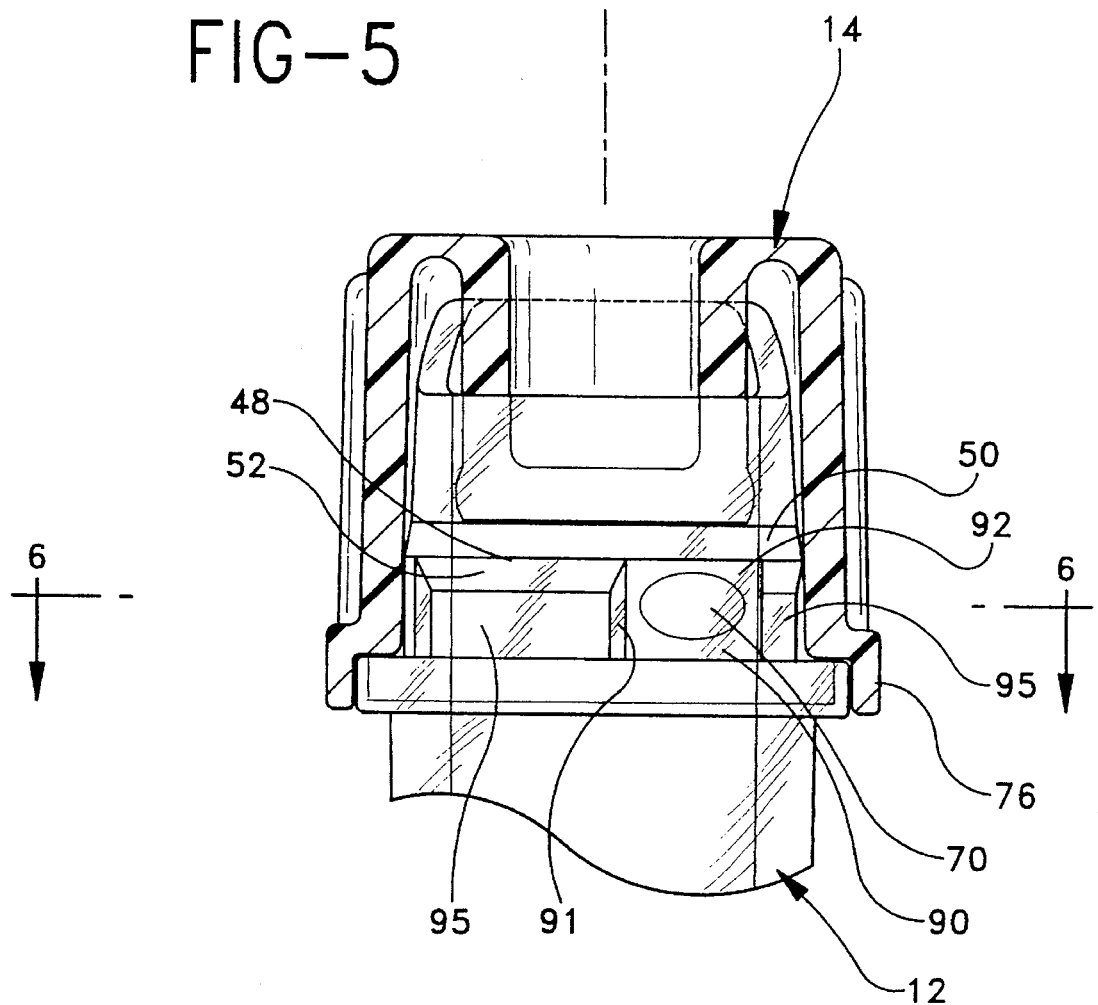
FIG. 5 is another enlarged cross-sectional view of the container and cap of FIG. 1, with the cap in the unlocked position.
Figure 6:
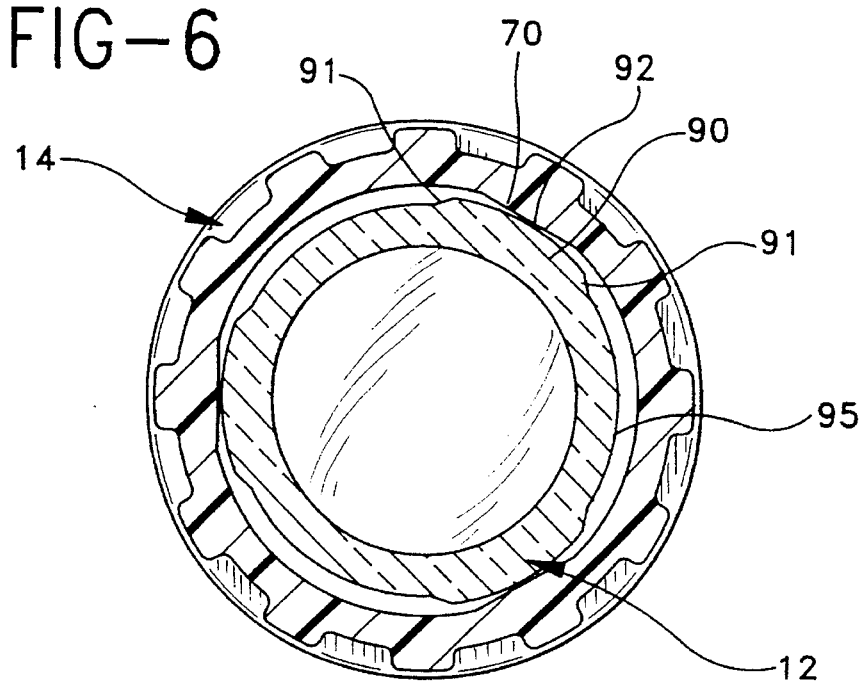
FIG. 6 is a cross-sectional view of the container and cap of FIG. 5, taken along line 6—6 thereof.

FIGS. 5 and 6 show container 12 with cap 14 in an unlocked position. More particularly, FIG. 5 is another cross-sectional view of collection assembly 10 and FIG. 6 is a cross-sectional view taken along line 6—6 in FIG. 5. As shown in FIGS. 5 and 6, cap 14 is unsecured from the container in a twist-off manner by applying a rotational force about a longitudinal axis 80 while holding container 12. Rotation of cap 14 with respect to container 12 causes protrusion 70 on cap 14 to climb out of indent 95 up incline 91 onto top surface 92 of riser 90, as shown in FIGS. 5 and 6. When protrusion 70 is in the location shown in FIGS. 5 and 6, cap 14 is unsecured from container 12 and can be slid off of container 12 since protrusion 70 is lifted to be level with the junction between upper edge 50 and lower edge 52 of locking ring 48 and merely has to be slid down upper edge 50. The rotational force applied to cap 14 to move protrusion 70 up onto riser 90 can be bi-directional, that is clockwise or counter-clockwise.

Figure 7:
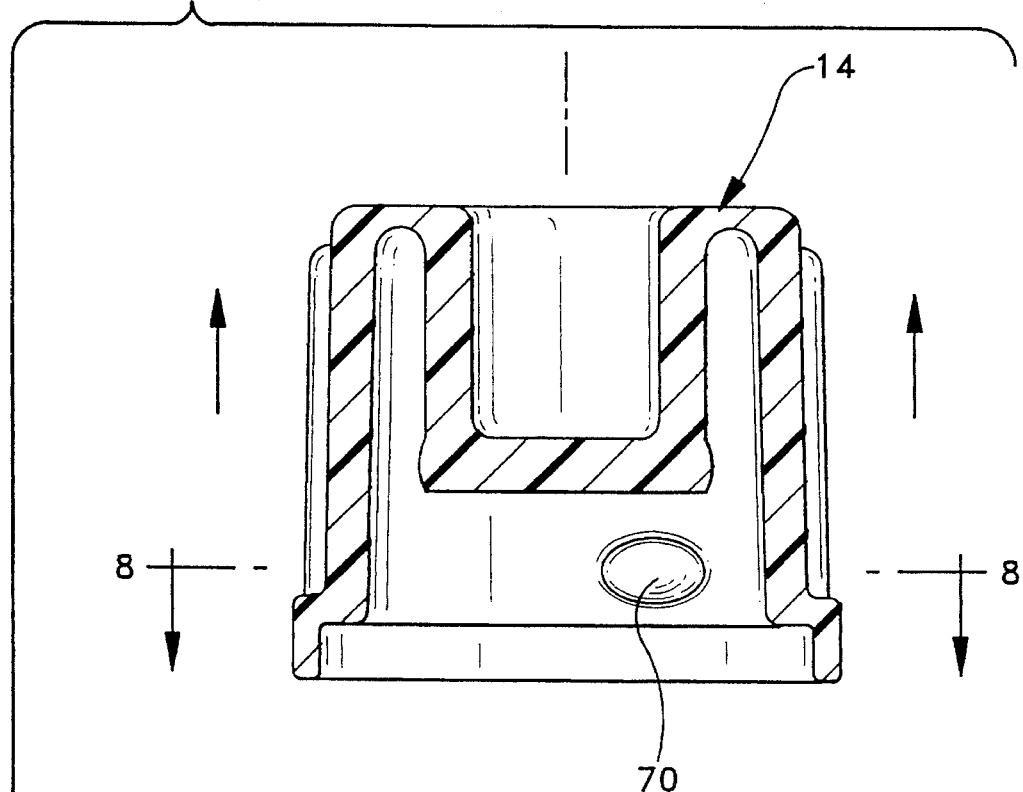
FIG. 7 is a cross-sectional view of the cap and a side elevational view of the container of FIG. 1.
Figure 7:
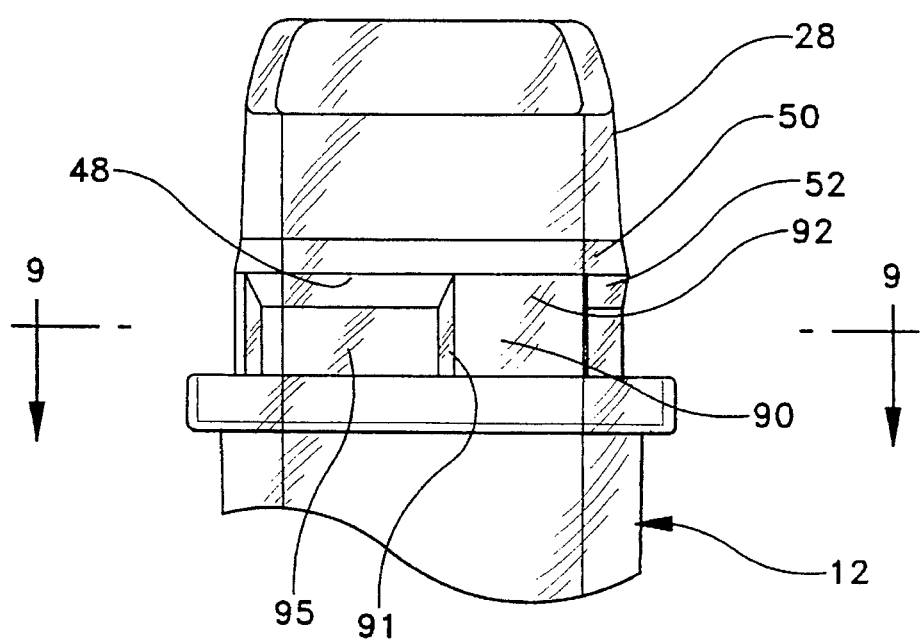
Figure 8:
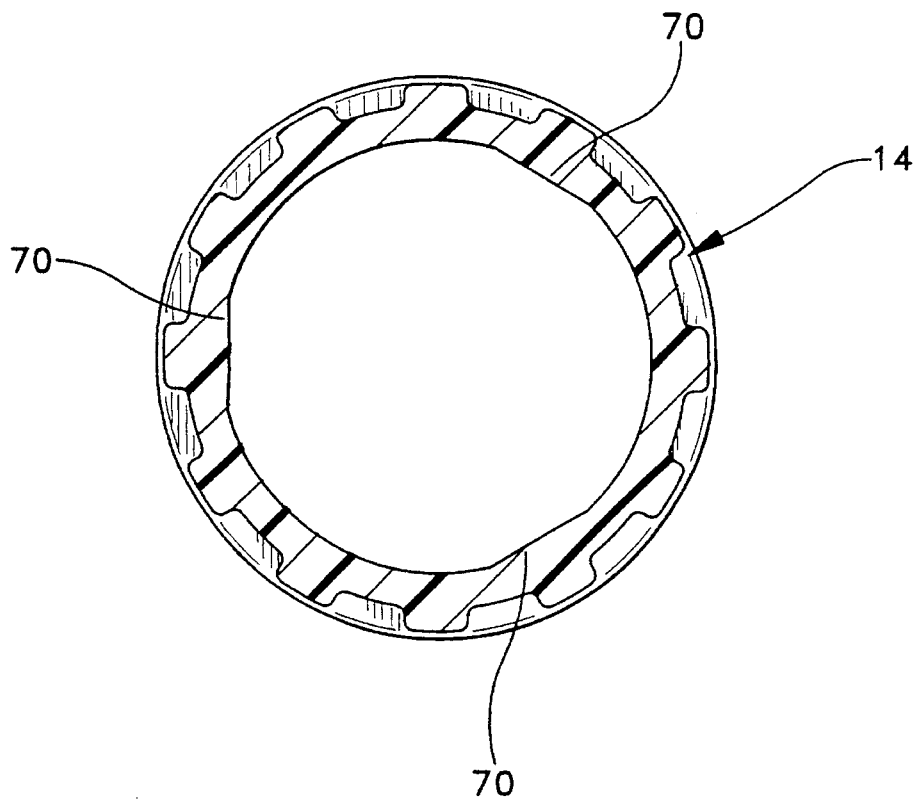
FIG. 8 is a cross-sectional view of the cap of FIG. 7, taken along line 8—8 thereof.
Figure 9:
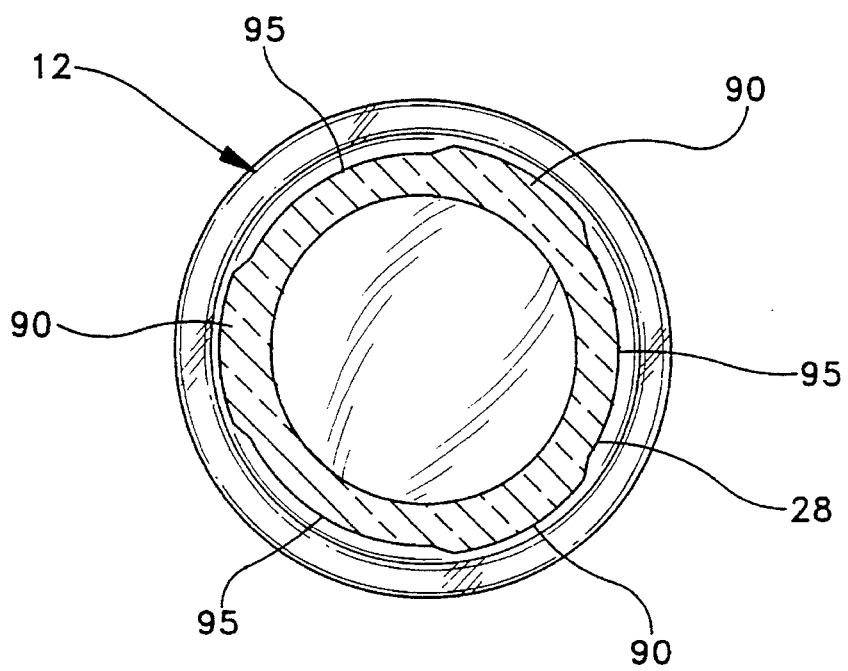
FIG. 9 is a cross-sectional view of the container of FIG. 7, taken along line 9—9 thereof.

FIGS. 7, 8 and 9 are various views of cap 14 and container 12, with cap 14 removed from container 12. More particularly, FIG. 8 is a cross-sectional view taken along line 8—8, and FIG. 9 is a cross-sectional view taken along line 9—9 in FIG. 7. These figures more clearly show the preferred embodiment of collection assembly 10 with three protrusions 70 on cap 14 and three risers on the outer surface of upper portion 28 of container 12.

The collection assembly of the invention may be made of a molded thermoplastic material so that the specimen collected may be readily viewed. Representative materials include, for example, polyethylene, polypropylene and polyvinyl chloride. The collection container may incorporate a hydrophilic material or a silicon, or a texture may be applied to the internal surface thereof for enhancing the flow and mixing of blood introduced into the container.

Although it is within the purview of the invention to provide caps which are colored to define specific forms of fluid collection containers containing materials for one reason or another or for defining the kind of examination to be conducted on the specimen collected, transparent caps may be provided. Also, it should be noted that the dimensions of the container are such as to provide space for labeling which may be important for identifying the collected specimens.

What is claimed is:

1. A collection assembly comprising:

a cap comprising a closed top portion and an open bottom portion; said cap further comprising:
  an outer skirt extending from said closed top portion to a bottom stop ledge at said open bottom portion and having an inner surface;
  a closed bottom inner skirt surrounded by said outer skirt and extending from said closed top portion toward said open bottom portion; and
  a solid protrusion extending from said inner surface of said outer skirt; and a container comprising an open top portion, a closed bottom portion and a side wall having an outer surface; said container further comprising:
  an integral lip extending from said open top portion;
  a cap seating flange on said outer surface of said container positioned where said integral lip extends from said top portion and containing a trough;
  a locking ring on said outer surface of said container positioned between said integral lip and said cap seating flange having an upper edge and a lower edge; and
  lifting means on said outer surface of said container positioned between said locking ring and said cap seating flange, said lifting means interacting with said solid protrusion on said cap to lift said solid protrusion over said locking ring and facilitate removal of said cap from said container upon rotation of said cap,
  wherein said solid protrusion bears against said locking ring of said container and said outer skirt on said cap extends over and beyond said trough in said cap seating flange so that said bottom stop ledge contacts said cap seating flange, when said cap is locked on said open top portion of said container.

2. The assembly of claim 1, wherein said lifting means comprises a riser located on said outer surface of said container positioned between said locking ring and said cap seating flange.

3. The assembly of claim 2, wherein said riser comprises a pair of inclines and a top surface, said top surface being flush with a junction between said upper edge and said lower edge of said locking ring to permit said solid protrusion on said cap to slid up one of said inclines onto said top surface and down an upper edge of said locking ring to facilitate removal of said cap from said container upon rotation of said cap.

4. The assembly of claim 1, wherein said cap further comprises a sealing ring on said closed inner skirt of said cap, wherein said sealing ring bears against said inner surface of said integral lip of said container when said cap is locked on said open top portion of said container.

5. The assembly of claim 1, wherein said lifting means comprises a plurality of risers located on said outer surface of said container, each of said risers being positioned between said locking ring and said cap seating flange.

6. The assembly of claim 5, wherein each of said plurality of risers comprises a pair of inclines and a top surface, said top surface being flush with a junction between said upper edge and said lower edge of said locking ring to permit said solid protrusion on said cap to slid up one of said inclines onto said top surface and down an upper edge of said locking ring to facilitate removal of said cap from said container upon rotation of said cap.

7. The assembly of claim 5, wherein said cap further comprises a sealing ring on said closed inner skirt of said cap, wherein said sealing ring bears against said inner surface of said integral lip of said container when said cap is locked on said open top portion of said container.

* * * * *